United States Patent [19]

Coulter

[11] Patent Number: 4,527,114
[45] Date of Patent: Jul. 2, 1985

[54] ELECTRICAL SLIT SCANNING APPARATUS

[75] Inventor: Wallace H. Coulter, Miami Springs, Fla.

[73] Assignee: Coulter Electronics, Inc., Hialeah, Fla.

[21] Appl. No.: 352,438

[22] Filed: Feb. 25, 1982

[51] Int. Cl.³ .................................... G01N 27/00
[52] U.S. Cl. ............................................... 324/71.1
[58] Field of Search ................... 324/71.1, 71.4; 377/10–12; 364/555

[56] References Cited

U.S. PATENT DOCUMENTS

| | | | |
|---|---|---|---|
| 2,656,508 | 10/1953 | Coulter | 324/71 |
| 3,390,326 | 6/1968 | Imadate | 324/71.4 |
| 3,502,973 | 3/1970 | Coulter et al. | 324/71 |
| 3,502,974 | 3/1970 | Coulter et al. | 324/71 |
| 3,657,537 | 4/1972 | Wheeless, Jr. et al. | 250/71 R |
| 3,668,531 | 6/1972 | Hogg | 328/150 |
| 3,701,029 | 10/1972 | Hogg | 324/71.1 |
| 3,720,470 | 3/1973 | Berkhan | 356/102 |
| 4,290,011 | 9/1981 | Berg et al. | 324/71.1 |
| 4,298,836 | 11/1981 | Groves et al. | 324/71 CP |

FOREIGN PATENT DOCUMENTS

WO80/00021 4/1980 PCT Int'l Appl.

Primary Examiner—Michael J. Tokar
Assistant Examiner—Kevin D. O'Shea
Attorney, Agent, or Firm—Gerald R. Hibnick

[57] ABSTRACT

A particle analyzer apparatus comprising a flow cell having a flow chamber wherein a flow of liquid suspension, having individual particles entrained therein, proceeds along a predetermined path; a pair of electrodes are disposed on opposed sides of the predetermined path, one of the electrodes having an end with a width parallel to the predetermined path that is less than the length of a given particle, the end of the electrode being positioned in close proximity to the predetermined path; energizing source for providing an electrical field between the pair of electrodes that traverses the predetermined path; and a particle pulse detector for detecting particle pulses caused by the particles passing through the electric field.

7 Claims, 3 Drawing Figures

ELECTRICAL SLIT SCANNING APPARATUS

FIELD OF THE INVENTION

The present invention relates to electrical volume sensing particle analyzers using the principle invented by Wallace H. Coulter for counting, sizing, and analyzing particles suspended in a liquid suspension.

BACKGROUND OF THE INVENTION

Since its conception more than 27 years ago, the principle of particle counting and sizing invented by Wallace H. Coulter has resulted in numerous improved methods and apparatuses for the electronic counting, sizing and analysis of microscopic particles, which are scanned in a fluid suspension of electrolyte, the first of which is shown by the pioneer U.S. Pat. No. 2,656,508 to Coulter. In this prior art particle analyzer, a D.C. electric current flow is established between two vessels by suspending electrodes in the respective bodies of the suspension fluid. The only fluid connection between the two bodies is through a microscopic orifice; hence, an electric current flow and field are established in and proximate to the orifice. The orifice and the resultant electric field in and around it constitute a sensing zone. As each particle passes through the sensing zone, for the duration of the passage, the electrical impedance of the contents of the sensing zone will change, thereby modulating the electric current flow and electric field in the sensing zone, and hence causing the generation of a signal to be applied to a detector suitably arranged to respond to such change.

In the commercial apparatus constructed in accordance with the heretofore mentioned U.S. Pat. No. 2,656,508, field excitation has been supplied by a direct current or low frequency source. The electrical change, i.e., D.C. signal, caused by the passage of a particle through the electric field of small dimensions, excited by a direct or low frequency current, is approximately proportional to particle size. A direct current is considered to be of zero frequency in this application. However, the impedance sensing principle has been expanded materially to provide information concerning particles being studied, not limited only to characteristics due to the size of particles, but including characteristics due to the composition and nature of the material constituting the particles, as disclosed in U.S. Pat. No. 3,502,974 to Coulter et al. and U.S. Pat. No. 3,502,973 to Coulter et al. These prior art apparatuses generally have at least two current sources, both of which are applied to the sensing zone simultaneously, one having a radio frequency (RF) and the other being the previously described "zero frequency" direct current (DC) or, alternatively, having a sufficiently low frequency that the reactive part of the particle impedance has a neglible effect on the response of the apparatus. One of the useful particle descriptors that can be obtained from this dual source arrangement is the "internal conductivity" or "opacity" of the particles. More specifically, with biological cells, their membranes have a very high resistivity in the range of a dielectric; however, the internal portion of the cell is fairly conductive. The RF current passes through the cell's membrane, thereby generating a detectable RF signal which correlates to the size, shape and conductivity of each particle. When the D.C. size signal for a cell is divided into the RF signal for that cell, a measurement termed "opacity" of the cell is obtained.

With the above described particle analyzers, the size and opacity measurements generally do not correlate exactly with the actual or true volume and internal electrical conductivity, respectively, of the cell. In apparatuses having hydrodynamic focusing, elongated particles will be aligned with their longitudinal axis substantially parallel to the axis of the sensing zone. With two equal volume particles, one being spherical and one being elongated, the spherical particle, while passing through the orifice, will have a greater cross section perpendicular to the current flow than the elongated particle. Hence, the spherical particle will distort the field in such a manner that it will give a greater measured size signal than the elongated particle, despite their equal volumes. Consequently, particles have been classified as to their shape by a term called "shape factor" which is used to correct their measured D.C. size signal. For instance, if an extremely elongated particle is assigned a shape factor of 1.0, then the spherical particle of the same volume has a shape factor of 1.5.

To correct for the inaccuracies introduced into the measured parameters by the particle's shape, the shape factor can be accurately measured on a cell by cell basis by obtaining a third signal, such as length, in addition to the RF and DC signals, and then correcting the measured parameters to obtain accurate values for the volume and internal conductivity of the cell, as described in U.S. Pat. No. 4,298,836, to Groves et al. However, this arrangement has the disadvantage of requiring an optical source and detector for obtaining the required length by making a "time of flight", i.e., length, measurement.

A drawback of the prior art electronic volume sensing particle analyzers is that slit scanning of the individual cell cannot be accomplished, such scanning being possible only with optical particle analyzers, as shown in U.S. Pat. No. 3,657,537 to Wheeless. More specifically, with the optical particle analyzers, a narrow illuminating beam, having a width less than the length of the cell traversing the same, excites fluorescence from a stained cell. In this manner the internal constituents of the cell are examined, such as the relative sizes of the cell's nucleus and cytoplasm. It is known that there are differences in internal conductivities of different portions of the cell, such as, for example, between the nucleus and the surrounding cytoplasm. However, in these prior art analyzers, these internal differences have not been measurable or subject to being quantified, due to the sensing zone created by the electric field of the sensing zone being always much longer in length than the cell. For instance, a sensing zone in a 75 micron long aperture will be substantially longer than the 75 microns and will frequently receive cells, such as red blood cells, having lengths in the range of 12 microns.

U.S. Pat. No. 3,720,470 to Berkhan discloses a flow chamber arrangement for moving particles along one side of the flow chamber's wall and PCT/EP80/0021 to Lindmo et al. discloses an arrangement for moving particles along the surface of a substrate. Previously mentioned U.S. Pat. No. 3,502,973 shows electrodes which create a wide electrical field that traverses the particle path.

The above described U.S. Pat. Nos. 3,502,973; 3,502,974; and 4,298,836 are incorporated by specific reference herein.

SUMMARY OF THE INVENTION

The present invention is directed to a particle analyzing apparatus comprising first means for providing a flow of liquid suspension, having individual particles entrained therein, along a predetermined path; energizing means, for generating an electric field, including a pair of electrodes disposed on opposed sides of the predetermined path, one of the electrodes having an end with a width parallel to the predetermined path that is less than the length of a given particle, the end of the electrode being positioned in close proximity to the predetermined path; and second means, electrically coupled to the energizing means, for detecting particle pulses caused by particles passing through the electric field.

The particle analyzer apparatus embodying the invention, when having electrical field with a high frequency, allows for the examination of continually differing, narrow portions of the cells. In this manner, the internal constituents of the particles, normally biological cells, can be examined. Additionally, when the electrical field is provided with a low frequency, the length of the individual particles can be determined.

BRIEF DESCRIPTION OF THE DRAWINGS

Further objects and advantages of the present invention will become apparent as the following description proceeds, taken in conjunction with the accompanying drawings in which.

DETAILED DESCRIPTION OF THE PREFERRED EMBODIMENT

Figure 1:
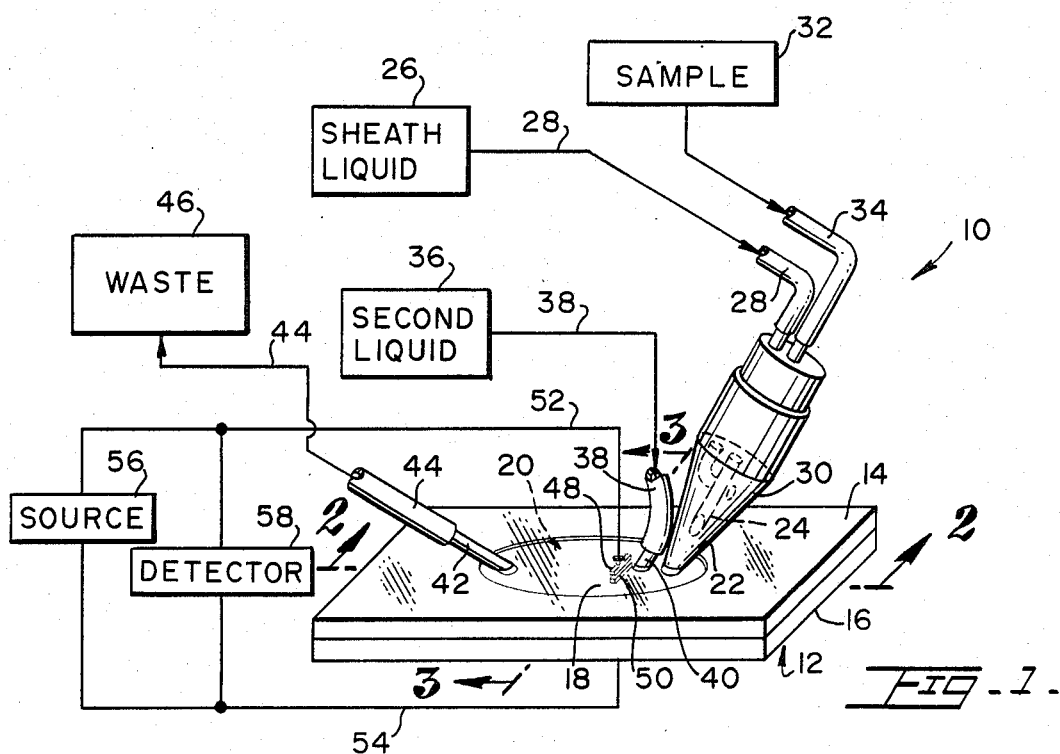
FIG. 1 shows a perspective view of the particle analyzing apparatus embodying the present invention.

As shown in FIG. 1, there is disclosed a particle analyzing apparatus 10 having a flow cell 12 formed from a first plastic plate 14 securely positioned on top of a second plastic plate 16. A circular cutout 18 is formed in the second plastic plate 16, so as to define a flow chamber 20.

A sheath tube 22 surrounds a sample introduction tube 24. A sheath liquid is introduced from a first pressurized reservoir 26 through a conduit 28 to an entry tube 30, so that the sheath liquid enters the sheath tube 22. A particle suspension of electrolyte is provided from a pressurized sample reservoir 32 through a conduit 34 to the sample introduction tube 24. In a well known manner, the sample suspension is hydrodynamically focused by the sheath liquid, so as to provide a laminar liquid jet from the end of the sheath tube 24 that proceeds in a direction toward a bottom surface of the flow chamber 20. A second liquid is provided under pressure from a pressurized liquid reservoir 36 through a conduit 38 to a tube 40. The liquid from the flow chamber 20 is removed through an exit tube 42, so as to pass through a conduit 44 to a waste reservoir 46, which is held to a negative pressure by a vacuum source (not shown).

A first electrode 48 is embedded in the first plastic plate 14 and a second electrode 50 is embedded below the first electrode 48 in the second plastic plate 16. The electrodes 48 and 50 are coupled by way of electrical conductors 52 and 54 respectively, to a parallel arrangement of an energizing source 56 and a particle pulse detector 58.

Figure 2:
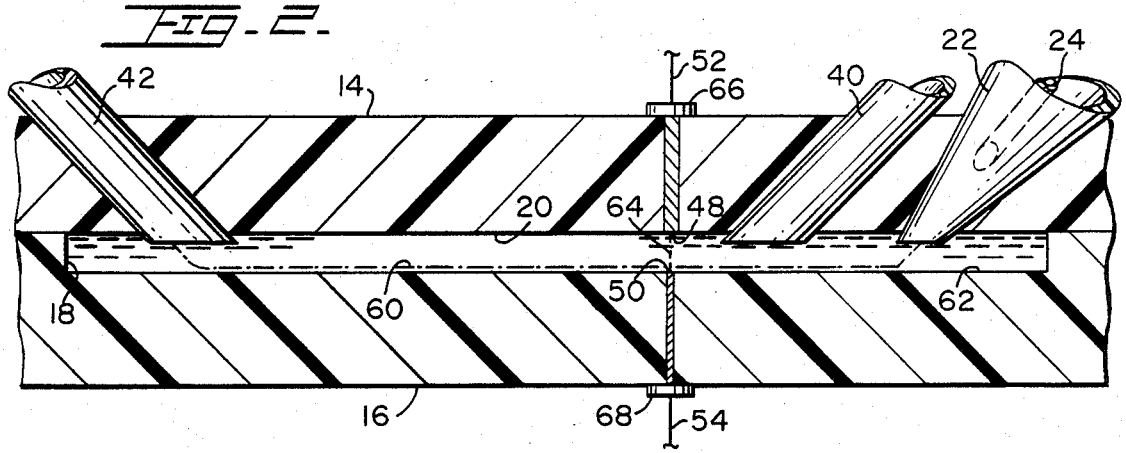
FIG. 2 shows a fragmentary, cross-sectional, side view of the particle analyzer apparatus taken along section line 2—2 in FIG. 1.
Figure 3:
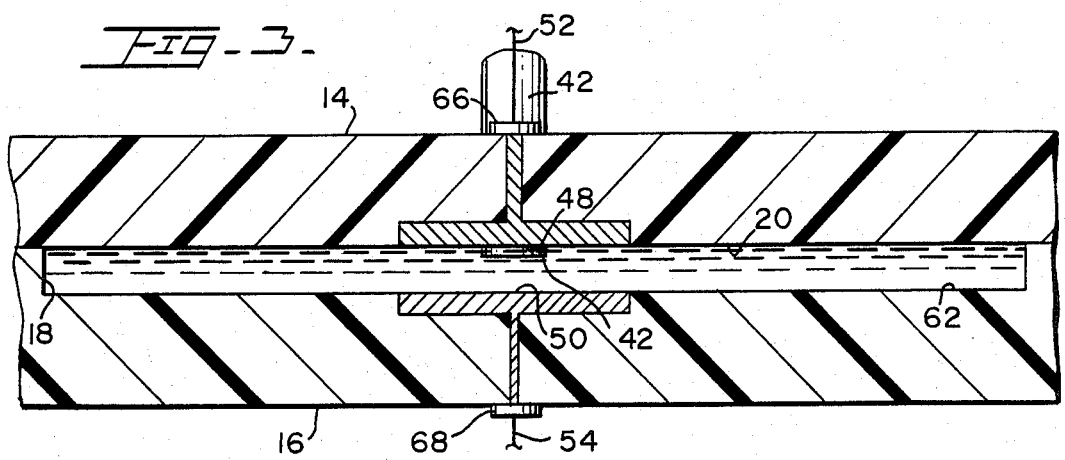
FIG. 3 shows a fragmentary, cross-sectional, side view of the particle analyzer apparatus taken along section line 3—3 in FIG. 1.

FIGS. 2 and 3 are fragmented views of the flow chamber 20 which shows the elements of the invention in more detail. The electrodes 48 and 50 are exaggerated in size to better illustrate the invention. The path of the particle suspension is shown by line 60. The particles exit from the sheath tube 22, proceed in a jet toward the lower surface 62 of the flow chamber, proceed along the surface 62 past the electrodes 48 and 50 and are subsequently removed through the exit tube 42.

The electrodes 48 and 50 are shown centered on a geometric plane 64, which is preferably perpendicular to the particle path 60. The second electrode 50 has a very narrow width along the particle path 60, as shown in FIG. 2. Preferably, but not necessarily, this width is about 2 to 3 microns. The first electrode 48 likewise should have a very narrow width, but is illustrated with a slightly broader width, to emphasize the fact that its width is not as critical and can be somewhat greater than that of the second electrode 50. The electrodes 48 and 50 have a pair of conductor contacts 66 and 68, respectively, formed on their outer ends. The flow chamber 20 can have a depth along plane 64 of, for example, 200 to 300 microns, although the depth is not critical and can vary substantially as desired.

In operation, the current lines from the end of the electrode 50 will leave at right angles to the electrodes surface and will traverse the particle path 60, so as to terminate on the first electrode 48. The present invention takes advantage of the fact that as the current lines leave the exposed surface of the electrode 50, at right angles therefrom, and proceed across the flow chamber without initially diverging or bulging to a significant degree. Hence, as the particles proceed through the sensing field, which is in close proximity to the lower surface 62, they pass through a very narrow field. For example, red blood cells, which have a length of approximately 12 microns, will pass through an electrical field having a width, along the particles path 60, that is shorter than the length of the cells. Hence, continually differing, narrow portions of the cells will be examined, when a high frequency current is used, as will be explained hereinafter. It is preferable to keep the current density fairly uniform in that portion of the plane 64 through which the particle passes; hence, the electrodes preferably have an elongated configuration parallel to the plane 64, as shown in FIG. 3. Consequently, slight variations from the particle path 60 along the surface 62 will not cause variations in the signal output.

As can be seen from above, it is desirable to keep the particles flowing as close as possible to the second electrode 50. Preferably, the second liquid is introduced through the tube 40 so as to maintain the particle path 60 immediately adjacent to the lower surface 62. Preferably, the pressure drops between the reservoirs 26 and 36 and between the reservoirs 36 and 46 are sufficient to cause the sheath and sample suspension to jet from the sheath tube 22 at a relatively high velocity, so as to cause the liquid of the jet to impact and spread out on the surface 62, thereby forcing the particles into very close proximity with the surface 62. In a well known manner, each of the reservoirs 26, 36, and 46 are held at progressively lower pressures, so that the liquid jets out of the sheath tube 22 and moves out of the chamber 20 through the exit tube 42. Moreover, the particles will remain hydrodynamically focused for several hundreds of microns along the particle path 60, after impacting on the surface 62. Consistent orientation of the particles allow for the extraction of improved cellular length information, as is well known. Hence, the electrodes 48 and 50 need to be in close proximity to the sheath tube 22. The flow system is basically the same as that shown in previously mentioned application PCT/EP80/0021, except the thin liquid layer, which includes the particles, is formed under a second liquid flow provided by the reservoir 36. With this arrangement, the particle path 60, in the electrical field, can be for example, under 10 microns from the surface 62. It should be understood that there are numerous ways in which those skilled in the art can use to move a stream of particles adjacent to one surface of a flow chamber, such as the flow chamber 20. For example, one alternative way is illustrated in the previously described U.S. Pat. No. 3,720,470. The invention herein resides in positioning a very narrow electrode closely adjacent to the particle path so as to create a very narrow electrical field for the particles to pass through.

The energizing source 56 and the particle pulse detector 58 can take the form of numerous prior art designs. Depending upon the desired application, the electrodes 48 and 50 can be energized by a low frequency source, including D.C., and/or a high frequency source, normally with radio frequencies, as taught in the incorporated U.S. Pat. Nos. 3,502,973 and 3,502,974. The high frequency or low frequency currents can provide useful measurements either by themselves or in combination.

Depending upon the intended use, the detector 58 can be used to detect and process particle pulses in many different, well known ways. The particle analyzing apparatus 10 is particularly useful in studying biological cells. For instance, when a D.C. current is provided by the source 56, the D.C. current lines must pass mostly around the outside of the cell; hence, the width of the particle pulses at a predetermined pulse threshold will represent the length of the cell. Likewise, integrating this signal will give a measurement of the cell volume. When the energizing source 56 provides a high frequency current, the high frequency current lines mostly pass through the cell, allowing for small, sequential segments of the cell to be scanned by the electrical sensing zone. In other words, continually differing, narrow portions of the cell are examined. The particle pulse signal received by the detector 58 can be used for examining the internal constituents of the cell. Use of both the high frequency and low frequency currents superimposed allows for the determination of internal conductivity of the cell, in accordance to the teachings of Incorporated U.S. Pat. No. 4,298,836. In such an application, the length of a cell, as determined by the pulse width, would be substituted for the optically determined length.

Preferably, the electrodes are formed of platinum, and can be etched into the surfaces of the flow chamber 20. The liquids in the reservoirs 26, 32 and 36 are electrolytes, such as a saline solution.

Although particular embodiments of the invention have been shown and described herein, there is no intention thereby to limit the invention to the details of such embodiments. On the contrary, the intention is to cover all modifications, alternatives, embodiments, usages and equivalents of the subject invention as fall within the spirit and scope of the invention, specification and the appended claims.

I claim:

1. A particle analyzer apparatus including resistive impedance sensing comprising:

first means for providing a flow of a liquid suspension of an electrolyte, said suspension having individual particles entrained therein, said first means forcing said flow to be along a predetermined path;

energizing means, for generating an electric field, including a pair of electrodes disposed on opposed sides of said predetermined path, one of said electrodes having an end with a width parallel to said predetermined path that is less than the length of a given particle for forming a very narrow electrical field, said end of said electrode being positioned in close proximity to said predetermined path so that each particle will flow through said very narrow electrical field; and second means, electrically coupled to said energizing means, for impedance detecting particle pulses caused by particles passing through said very narrow electrical field.

2. The particle analyzer apparatus according to claim 1, wherein said first means includes a flow cell having a flow chamber, said pair of electrodes are mounted in opposed walls of said flow chamber, and the liquid suspension is forced into said flow chamber so the said predtermined path is caused to lie close to the one of said opposed walls to which is mounted said one electrode.

3. The particle analyzer apparatus according to claim 2, wherein said electrode, which is in close proximity to said predetermined path, is embedded in said flow cell with said end being flush to said wall of said flow chamber.

4. The particle analyzer apparatus according to any one of claims 1, 2 or 3, wherein said energizing means provides said electrical field with a low frequency.

5. The particle analyzer apparatus according to any one of claims 1, 2 or 3, wherein said energizing means provides said electrical field with a high frequency for causing said electrical field mostly to pass through said particles, whereby continually differing portions of said given particle are examined.

6. The particle analyzer apparatus according to claim 4, wherein said energizing means provides said electrical field with a high frequency for causing said electrical field to pass through said particles, whereby continually differing portions of said given particle are examined.

7. The particle analyzer apparatus according to any one of claims 1, 2, or 3, wherein said first means includes means for hydrodynamically focusing the particles as the particles pass through said electrical field.

* * * * *